United States Patent [19]

Akkerman et al.

[11] 4,128,548
[45] Dec. 5, 1978

[54] PROCESS FOR PREPARING 6,7-BENZOMORPHANS

[75] Inventors: Antony M. Akkerman; Geertruida C. van Leeuwen, both of Amsterdam, Netherlands

[73] Assignee: ACF Chemiefarma N.V., Maarssen, Netherlands

[21] Appl. No.: 658,739

[22] Filed: Feb. 17, 1976

[30] Foreign Application Priority Data

Feb. 25, 1975 [GB] United Kingdom ............. 7891/75

[51] Int. Cl.² .......................................... C07D 221/26
[52] U.S. Cl. ............................. 542/429; 260/345.9 R; 260/556 AR; 260/570.5 R; 260/570.5 CA; 546/97; 542/430
[58] Field of Search ................. 260/291.54, DIG. 13, 260/293.54

[56] References Cited

U.S. PATENT DOCUMENTS

| 3,138,603 | 6/1964 | May ............................. 260/294.3 |
| 3,372,165 | 3/1968 | Archer ......................... 260/294.7 |
| 3,764,606 | 10/1973 | Akkerman et al. ......... 260/293.54 |
| 3,969,468 | 7/1976 | Tamaki et al. ............. 260/293.54 |

OTHER PUBLICATIONS

Sethna, S. in Olah, G., Friedel–Crafts and Related Reactions, vol. III, Part II, Interscience, New York, 1964, pp. 911–915.

Morrison, R., et al., Organic Chemistry, Allyn and Bacon, Inc., Boston, 1959, pp. 417–418.

Primary Examiner—Henry R. Jiles
Assistant Examiner—Richard A. Schwartz
Attorney, Agent, or Firm—Curtis, Morris & Safford

[57] ABSTRACT

The invention is concerned with certain novel 6,7-benzomorphan derivatives having analgesic and/or morphine-antagonistic properties of the formula

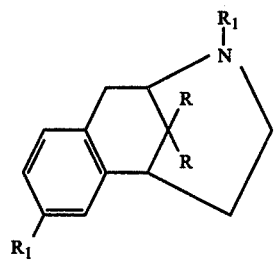

wherein each R is a lower alkyl group; $R_1$ is a hydrogen atom, or an alkyl, haloalkyl, alkenyl, haloalkenyl, alkinyl, cycloalkyl, cycloalkenyl, cycloalkylalkyl, cycloalkenylalkyl, cycloalkylidenealkyl, aralkyl, heteroarylalkyl or heterocycloalkylalkyl group; $R_2$ is a hydrogen atom or a hydroxy, alkoxy, alkoxyalkoxy or acyloxy group.

Such 6,7-benzomorphans may be in the form of their optically active enantiomers and/or their therapeutically acceptable salts. Methods for producing such 6,7-benzomorphan derivatives, and novel intermediates useful for such production are also disclosed and form part of the invention.

6 Claims, No Drawings

PROCESS FOR PREPARING 6,7-BENZOMORPHANS

This invention is concerned with certain novel 6,7-benzomorphan derivatives, with methods for their preparation, and with certain novel intermediates.

Certain 6,7-benzomorphans have previously been synthesized (E. L. May and J. G. Murphy, J.Org.Chem. 20, 257 (1955)) and tested as possible analgesics. Some benzomorphans have been successfully used in medicine, see e.g. N. B. Eddy and E. L. May in International Series of Monographs in Organic Chemistry, Vol. 8 Part II (B), Pergamon Press (1966); A. F. Casy in Progress in Medicinal Chemistry, Vol. 7 (2) 229 (1970), Butterworths; H. W. Kosterlitz, H. O. J. Collier and J. E. Villarreal, "Agonist and Antagonist actions of narcotic analgesic drugs", McMillan (1972). Usually, these 6,7-benzomorphans possess a quaternary carbon atom at the 5-position, while the 9-position is substituted by one single methyl or ethyl group. (By "quaternary carbon atom" we mean a carbon atom having all four valencies bound to carbon atoms not belonging to functional groups).

6,7-Benzomorphans have also been described which are devoid of a substituent at the 5-position but possess one single substituent at the 9-position (T. Oh-Ishi, A. E. Jacobson, R. S. Wilson, H. J. C. Yek and E. L. May, J. Org. Chem. 39, 1347 (1974)). These compounds do not contain any quaternary carbon atom, as is also the case with 6,7-benzomorphans which carry no substituents either at the 5-position or at the 9-position, and which have been described e.g. by K. Kanematsu, R. T. Parfitt, A. E. Jacobson, J. H. Ager and E. L. May, J. Am. Chem. Soc. 90, 1064 (1968); K. Kanematsu, M. Takeda, A. E. Jacobson and E. L. May, J. Med. Chem. 12, 405 (1969); K. Mitsuhashi, S. Shiotani, R. Oh-Uchi and H. Shiraki, Chem. Pharm. Bull. 17, 434 (1969); M. Takeda, A. E. Jacobson, K. Kanematsu and E. L. May, J. Org. Chem. 34, 4154 (1969); E. L. May and M. Takeda, J. Med. Chem. 13, 805 (1970).

6,7-Benzomorphans with quaternary carbon atoms both at the 5- and the 9-position are known from our Dutch patent application No. 69.08529 and the corresponding British Pat. No. 1,299,669. In this Dutch specification, we have apparently described 6,7-benzomorphans with only one quaternary carbon atom at position 9. Their preparation is given in Examples 8 and 9 of the Dutch specification. However, since filing that application, we have realised that the compounds obtained in these two Examples do not have the structure proposed at that time. In fact, in the reactions described in Examples 8 and 9 of the Dutch specification, a rearrangement takes place with the result that the compounds formed are isomers of the desired 6,7-benzomorphans. Thus, Examples 8 and 9 are incorrect and the Dutch patent application No. 69.08529 is only concerned with 6,7-benzomorphans having two quaternary carbon atoms.

We have now found that certain 6,7-benzomorphan derivatives in which the carbon atom at the 9-position is quaternary and the carbon atom at the 5-position carries a hydrogen atom, have useful pharmaceutical properties. These derivatives comprise compounds of the formula

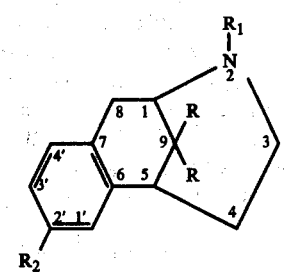

wherein each R is a lower (i.e. up to 6 carbon atoms) alkyl group, preferably methyl; $R_1$ is a hydrogen atom or an alkyl, haloalkyl, alkenyl, haloalkenyl, alkinyl, cycloalkyl, cycloalkenyl, cycloalkylalkyl, cycloalkenylalkyl, cycloalkylidenealkyl, aralkyl, heteroarylalkyl or heterocycloalkylalkyl group; $R_2$ is hydrogen or a hydroxy, alkoxy, alkoxyalkoxy or acyloxy group; and pharmaceutically acceptable salts thereof. The optical isomers of these compounds are also included.

These compounds are novel and form one aspect of the present invention. They are collectively hereinafter referred to as "the compounds of the invention".

Among the preferred compounds are those in which R is methyl, $R_2$ is hydroxy and:
(a) $R_1$ is hydrogen;
(b) $R_1$ is methyl, particularly the (−)-enantiomers of such derivatives;
(c) $R_1$ is —$CH_2$—CH=$CH_2$, particularly the (−)-enantiomers of such derivatives;
(d) $R_1$ is —$CH_2$—(cyclobutyl); or
(e) $R_1$ is tetrahydrofurfuryl.

We have found that, dependent on the nature of the substituents (primarily $R_1$), the compounds of the invention may possess not only central-analgesic or morphine-antagonistic activity, but also a combination of these properties. Those compounds which show the combination of properties can be considered as analgesics with a much lower chance of development of tolerance and addiction than the usual morphine-like drugs.

The compounds of formula I in which R is methyl, $R_2$ is hydroxy and $R_1$ is hydrogen have a low pharmacological activity, but they are among the preferred compounds of the invention because they are particularly useful as intermediates in the preparation of other compounds of the invention.

The invention also includes a pharmaceutical composition which comprises a compound of the invention and an inert pharmaceutically acceptable diluent or carrier therefor.

The compounds of the invention may be prepared by a process which comprises subjecting to a ring closure reaction a tetrahydronaphthalene derivative of the formula:

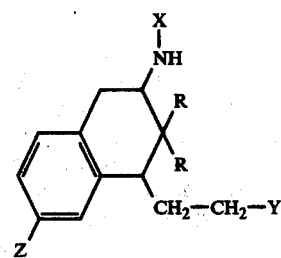

wherein R is as defined above, Y is a replaceable atom or group, X is $R_1$ as defined above or is an atom or group substitutable by $R_1$, and Z is $R_2$ as defined above or is an atom or group substitutable by $R_2$; treating the compound so formed as necessary to substitute the desired $R_1$ and/or $R_2$ for X and/or Z respectively; and, if desired, forming a salt of the compound so formed. Y is preferably a replaceable halogen atom, particularly a chlorine atom.

A preferred starting material in this process has the formula:

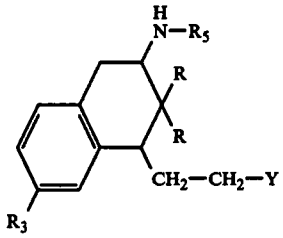

XVII wherein R and Y are as defined above, $R_3$ is hydrogen or a lower alkoxy group, and $R_5$ is an alkyl, cycloalkyl or cycloalkylalkyl group.

In the process of the present invention, the 6,7-benzomorphan ring system:

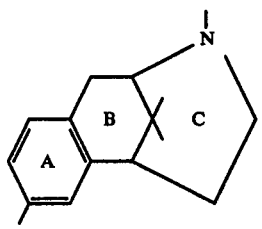

II is obtained by building up ring C as the last stage in a series of steps, directed at ring closure of the 1-(β-haloethyl)-3-amino-1,2,3,4-tetrahydronaphthalene derivatives of formula III, in which Y represents a halogen atom.

The compounds of formula III may be made from 3-amido-3,4-dihydro-1(2H)-naphthalenone derivatives of the formula:

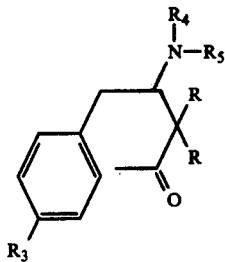

IV in which R is as defined above and is preferably a methyl group, $R_3$ is a hydrogen atom or a lower alkoxy group, $R_4$ is an acyl group, preferably a substituted sulphonyl group, in particular a p-toluene-sulphonyl group, and $R_5$ is an alkyl, cycloalkyl or cycloalkylalkyl group. Preferably, $R_5$ is an alkyl group, in particular a methyl group. It will be clear to those skilled in the art that $R_5$ may also represent other substituents insofar as they are not labile in the synthetic procedures and do not interfere with them.

The compounds of formula IV can be converted into the compounds of formula III by a. reacting them with an alkali metal acetylide to form a compound of formula:

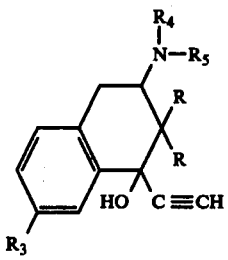

X b. partially reducing the ethinyl group to form a compound of formula:

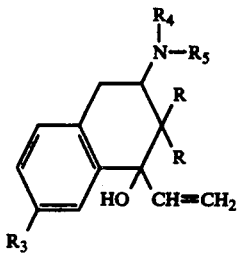

XI c. isomerising the compound of formula XI with dilute acid to form the compound of formula:

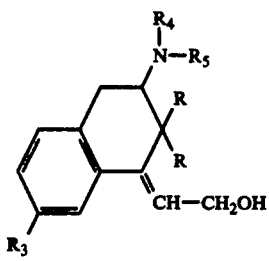

XII d. either converting the compound of formula XII directly, by reduction, into the compound of formula:

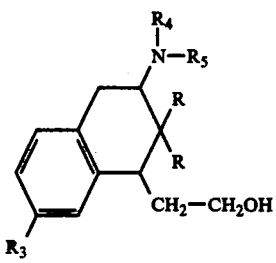

XIII or converting the compound of formula XII into the tetrahydropyranyl ether of formula:

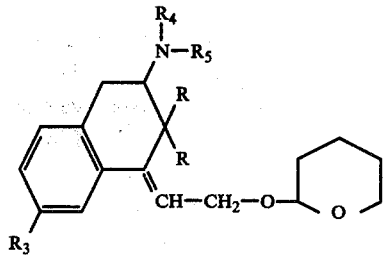

and then reducing the compound of formula XIV to form

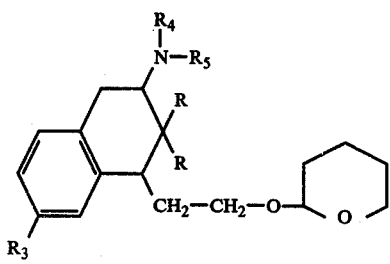

and, if desired, acid hydrolyzing compound XV to form compound XIII, deacylating compound XIII to form the aminoalcohol XVI; or deacylating compound XV, followed by hydrolyzing to form the aminoalcohol compound

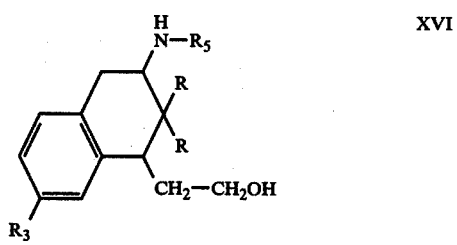

Compound XII may alternatively be deacylated under mild reducing conditions with concomitant saturation of the olefinic bond to form the aminoalcohol XVI. The aminoalcohol XVI is then converted into the desired compound of formula III.

The compounds of formula IV are novel, as are the compounds of formula XVII.

The compounds of formula IV may be prepared by a. acylating an aminoacid ester of the formula:

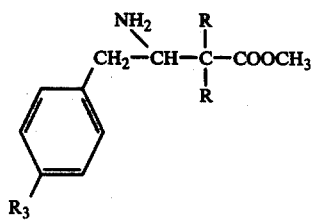

to form the corresponding acylamino ester of the formula:

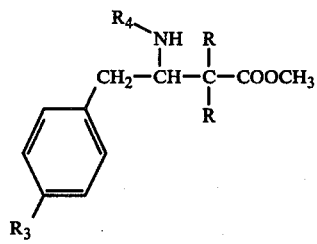

b. if desired, alkylating the ester of formula VI to form the alkylamido ester

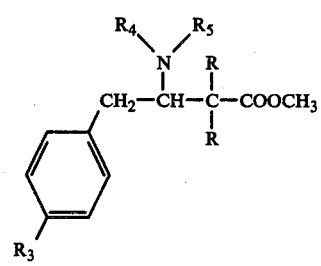

c. saponifying the ester VI or VII to form

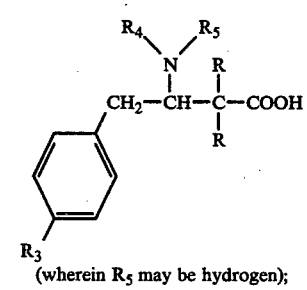

(wherein $R_5$ may be hydrogen);

d. converting the compound of formula VIII into the amidoacyl chloride of formula:

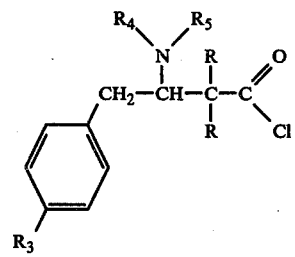

e. converting the compound of formula IX by ring closure into a compound of formula IV. The compounds in which $R_5$ is a hydrogen atom can then be alkylated if desired.

In the above process for preparing the compounds of formula IV, the amino acid ester V (which is described in Dutch specification No. 69.08527) is acylated in the usual manner for such compounds to form the acylamino ester VI. The amido function of this ester may then be alkylated with an alkyl halide in the presence of a base, such as sodium hydride, in a suitable solvent such as benzene or dimethyl formamide, to give the ester VII.

Compound IX is reacted in the presence of a Friedel-Crafts catalyst to cause ring closure to form the 3-amido-3,4-dihydro-1(2H)-naphthalenone derivative of formula IV. It will be clear that, if the alkylation of compound VI is omitted, but the subsequent steps are still carried out, this will result in a compound IV in which $R_5$ represents a hydrogen atom. In the next step of the synthesis of the compounds of the invention, however, it is desirable that compound IV should not contain an active hydrogen atom, so that when $R_5$ is hydrogen, this atom is preferably substituted by another $R_5$ group.

In the process described above for converting compounds of formula IV to compounds of formula III, the compounds IV are first reacted with an alkali metal compound of acetylene, preferably lithium acetylide which is preferably complexed with ethylene-diamine, to form the adduct X. The ethinyl group of compound X is now partially reduced to a vinyl group, thus giving compound XI, which possesses an allylic alcohol function. This partial reduction is preferably carried out by catalytic hydrogenation with palladium on calcium carbonate as the catalyst. The best results are obtained if palladium on coal is also present.

Under the influence of dilute acid, compound XI suffers an allylic rearrangement to form compound XII, which is also an allyl alcohol but has a terminal hydroxyl group. A suitable medium for this rearrangement is a mixture of dilute aqueous sulphuric acid and dioxane. The formation of the unsaturated alcohol XII from the ketone IV as herein described may be considered as a variant of Dimroth's method for the synthesis of cycloalkylidene ethanols from cycloalkanones (K. Dimroth, Ber. 71, 1333 (1938)).

Reduction of compound XII by catalytic hydrogenation, results in saturation of the exocyclic double bond, giving compound XIII. Under certain circumstances this hydrogenation also leads to the reduction of the terminal hydroxyl group and a product is generated containing an ethyl group at position 1, instead of a β-hydroxyethyl group. This will be the case, for example, when the hydrogenation is carried out with platinum oxide as the catalyst and alcohol as the solvent. This undesired hydrogenolysis may be suppressed by carrying out the hydrogenation in a basic medium, e.g. in the presence of an organic base such as triethylamine. Also, good results may be obtained if compound XII is first converted into the tetrahydropyranyl ether of formula XIV, and then hydrogenated with e.g. palladium as a catalyst. From the reduced ether XV, the β-hydroxyethyl compound XIII is formed by acidic hydrolysis.

Compound XV — and other compounds in the synthesis originating therefrom — possess two asymmetric carbon atoms ($C_1$ and $C_3$), thus forming a mixture of two diastereoisomers. These are not separated but are subjected to a reaction in which the acyl group $R_4$ is split off. For that purpose, mild reaction conditions are required, because the amido group tends to leave with formation of a double bond between carbon atoms $C_3$ and $C_4$. The acyl group preferred in this synthesis, arylsulphonyl, particularly p-toluenesulphonyl, can be removed reductively under mild conditions. An appropriate method for the deacylation of compound XIII or XV is by reaction with an alkali metal, preferably sodium, in liquid ammonia. The removal of the acyl group from compound XIII forms the aminoalcohol XVI. The removal of the acyl group from compound XV, followed by acidic hydrolytic removal of the tetrahydropyranyl group also forms the aminoalcohol XVI. The aminoalcohol XVI in each case is formed as a mixture of two diastereoisomers.

An additional possibility, which is in fact the shortest way to reach compound XVI, is the reduction of the double bond and the concomitant reductive removal of the arylsulphonyl group in compound XII by means of the above mentioned technique namely reduction with an alkali metal dissolving in liquid ammonia.

The aminoalcohol XVI is treated to replace the hydroxyl group by a halogen atom Y. Advantageously thionyl chloride may be used, which converts the hydrochloride of compound XVI, dissolved in an inert solvent such as chloroform, into the reaction product:

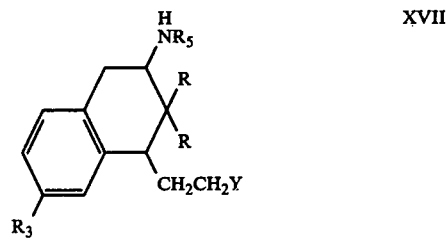

XVII consisting of the hydrochlorides of two diastereoisomeric 1-(β-chloroethyl)-3-amino-1,2,3,4-tetrahydronaphthalene derivatives, in which R, $R_3$ and $R_5$ are as defined above and Y is a replaceable atom or group, preferably a halogen atom, particularly a chlorine atom. Compound XVII, in which Y=Cl, with substituents on $C_1$ and $C_3$ is the trans-position, does not lend itself to ring closure to form the 6,7-benzomorphan ring system. However, because its hydrochloride is less soluble in chloroform than is the cis-diastereoisomer, this useless isomer can be largely removed from the mixture by filtration.

If the remaining solution is then made alkaline, the available cis-isomer of compound XVII cyclisizes easily to form the 6,7-benzomorphan with formula:

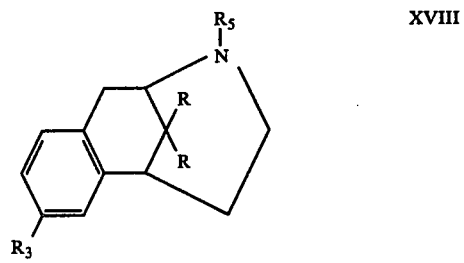

XVIII while any trans-isomer of compound XVII still present remains unchanged. Separation and purification may be effected by crystallization of the hydrochlorides. In compound XVIII, R, $R_3$ and $R_5$ are as defined above. Compounds in which R represents a methyl group, $R_3$ a hydrogen atom or a methoxy group and $R_5$ a methyl group, however, are preferred, particularly if $R_3$ is a methoxy group, cf. formula XIX:

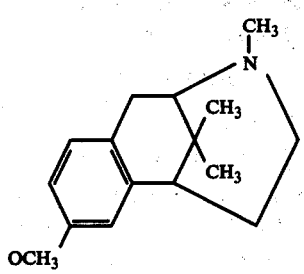

Compound XVIII, e.g. the preferred compound XIX, can be converted into 6,7-benzomorphan derivatives of formula I as follows. Compound XIX can be converted into the compound according to formula I in which R and $R_1$ are methyl groups and $R_2$ is a hydroxyl group, by treating compound XIX with an ether splitting agent, such as hydrogen bromide or hydrogen iodide. Compound XIX may also be treated with an agent which removes the methyl group from the amino group. Cyanogen bromide, which is common for that purpose in benzomorphan chemistry, may be used here, giving a compound according to formula I, in which R is a methyl group, $R_1$ a hydrogen atom and $R_2$ a methoxy group, represented by formula XX:

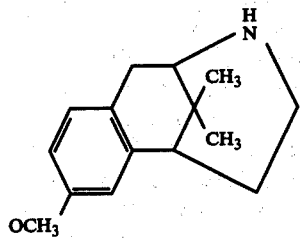

In compound XX, substituents may be introduced on the nitrogen atom with the indicated meaning for $R_1$ (except hydrogen), by direct alkylation with alkyl halides or, indirectly, by acylation with acyl halides, followed by reduction of the acyl groups to alkyl groups by means of complex metal hydrides such as lithium aluminium hydride. Both methods are common in benzomorphan chemistry (Dutch patent application 69.08529). Thus, compounds of formula XXI:

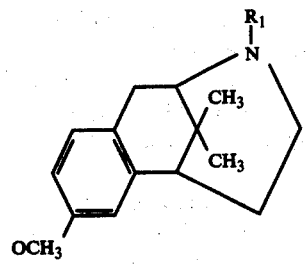

are formed in which $R_1$ has the above-mentioned meaning (except hydrogen).

The methoxy group in the compounds of formula XXI may be replaced by substituents with the indicated meanings for $R_2$, by first converting the methoxy group into a hydroxyl group and then, if necessary, alkylating or acylating the hydroxyl group, or eliminating the hydroxyl group by reduction (see for instance W. J. Musliner and J. W. Gates, J. Am. Chem. Soc. 88, 4271 (1966) and E. Vowinkel and Ch. Wolff, Chem. Ber. 107, 907 (1974)). It is also possible to convert first the methoxy group into a hydroxyl group, before introducing substituent $R_1$ as indicated above, and to alkylate or acylate the hydroxyl group subsequently, if necessary. In both cases 6,7-benzomorphan derivatives according to formula I are obtained, in which R represents a methyl group, $R_1$ is as defined above (except hydrogen) and $R_2$ is as defined above.

Because, in the 6,7-benzomorphan ring system, the piperidine ring can only be attached in a cis manner to the tetrahydronaphthalene nucleus, compounds according to formula I can only exist in one racemic form, in spite of the presence of two asymmetric carbon atoms.

By resolution into antipodes one laevo and one dextro enantiomer can be obtained from compounds according to formula I. These enantiomers form also part of the invention. To obtain these optically active enantiomers, preferably compounds with $R_1$=H are resolved, followed by substitution on the nitrogen atom according to the above-mentioned methods. For the resolution itself optically active acids, such as (+) and (−) tartaric acid, may be used.

In order that the invention may be more fully understood, the following Examples are given by way of illustration only. Examples 1 to 14 illustrate the preparation of intermediates.

EXAMPLE 1

Methyl 2,2-dimethyl-4-(p-methoxyphenyl)-3-(p-toluenesulphonamido)butyrate

To a solution of 251 g of methyl 3-amino-2,2-dimethyl-4-(p-methoxyphenyl)butyrate and 121 g of triethylamine in 750 ml of chloroform, there is added, with mechanical stirring and cooling with ice water, a solution of 210 g of p-toluenesulphonyl chloride in 500 ml of chloroform. After completion of the addition, which is carried out at such a rate that the temperature of the reaction mixture does not exceed 25° C., stirring is continued for 1.5 hours. Then the solution is washed with water, dilute hydrochloric acid and again with water, subsequently. After drying, the organic solvent is stripped off in vacuo. The residue is treated with ether, resulting in the crystallization of the title compound.

White crystals, melting point 126°-127° C. Yield 85%.

EXAMPLE 2

Methyl 2,2-dimethyl-4-(p-methoxyphenyl)-3-(N-methyl-p-toluenesulphonamido)butyrate A solution of 405 g of methyl 2,2-dimethyl-4-(p-methoxyphenyl)-3-(p-toluenesulphonamido)butyrate in 1800 ml of dry dimethylformamide is added to a mechanically stirred suspension of 52.8 g of sodium hydride in 320 ml of the same solvent. After the reaction mixture has been heated at 80° C. for 1 hour it is cooled when 93 ml of methyl iodide is added. After an additional period of heating (under reflux) the mixture, after being cooled, is poured into plenty of water. A white crystallisate separates. After filtration and drying it melts at 132°-134° C. Yield 96%.

EXAMPLE 3

2,2-Dimethyl-4-(p-methoxyphenyl)-3-(N-methyl-p-toluenesulphonamido)butyric acid

A solution of 418 g of methyl 2,2-dimethyl-4-(p-methoxyphenyl)-3-(N-methyl-p-toluenesulfonamido)-butyrate in 2350 ml of ethanol is mixed with a solution of 248 g of potassium hydroxide in 370 ml of water. After boiling the mixture for 4 hours it is cooled and acidified by the addition of 6 N hydrochloric acid.

The title compound separates as white crystals melting at 175°–176° C. Yield 96%.

EXAMPLE 4

2,2-Dimethyl-4-(p-methoxyphenyl)-3-(N-methyl-p-toluenesulfonamido)butyryl chloride

A mixture of 283 g of 2,2-dimethyl-4-(p-methoxyphenyl)-3-(N-methyl-p-toluenesulfonamido)butyric acid, 1500 ml of dry benzene and 430 ml of thionyl chloride is boiled for 3 hours. After removal of volatile material by evaporation in vacuo, the residue is taken up in toluene and the solvent is evaporated in vacuo. This procedure is repeated twice whereafter crystallization of the initially oily product is accomplished by treatment with ether, melting point 110°–111° C.

EXAMPLE 5

3,4-Dihydro-2,2-dimethyl-7-methoxy-3-(N-methyl-p-toluenesulfonamido)-1(2H)-naphthalenone

To a cooled (with ice water) and stirred solution of 256 g of 2,2-dimethyl-4-(p-methoxyphenyl)-3-(N-methyl-p-toluenesulfonamido)butyryl chloride in 1500 ml of dry benzene 195 g of aluminium chloride is added rather rapidly. The mixture is stirred at room temperature for an additional 25 minutes and then poured on to a mixture of ice and 950 ml of concentrated hydrochloric acid. After stirring the mixture at room temperature for 30 minutes the organic layer is separated whereas the aqueous layer is shaken twice with benzene. The combined organic solutions are washed twice with water and again twice with an aqueous solution of potassium carbonate whereupon, after drying, the whole is concentrated in vacuo. The residue is taken up in ether which brings about the crystallization of the title product.

White crystals melting at 119°–120° C. Yield 82%.

EXAMPLE 6

2,2-Dimethyl-1-ethinyl-7-methoxy-3-(N-methyl-p-toluenesulphonamido)-1,2,3,4-tetrahydro-1-naphthol

A suspension of 100 g of lithium acetylide-ethylenediamine in 1400 ml of dry tetrahydrofuran is saturated with acetylene. To this suspension, which is mechanically stirred and flushed continuously with acetylene, there is added a solution of 230 g of 3,4-dihydro-2,2-dimethyl-7-methoxy-3-(N-methyl-p-toluenesulphonamido)-1(2H)-naphthalenone in 650 ml of dry tetrahydrofuran. The addition takes some 20 minutes, the temperature of the mixture being kept at 25°–30° C.

After elapse of an additional 30 minutes the reaction mixture is poured into a solution of 160 g of ammonium chloride in 1500 ml of water. The products of the reaction are extracted from the mixture by means of shaking with chloroform. The chloroform layer is washed with dilute hydrochloric acid and again twice with water. After being dried the organic solution is evaporated in vacuo, leaving a residue which is dissolved in ether. From this solution the product separates as white crystals melting at 148°–150° C. Yield 90%.

EXAMPLE 7

2,2-Dimethyl-7-methoxy-3-(N-methyl-p-toluenesulphonamido)-1,2,3,4-tetrahydro-1-vinyl-1-naphthol

A mixture of 205 g of 2,2-dimethyl-1-ethinyl-7-methoxy-3-(N-methyl-p-toluenesulphonamido)-1,2,3,4-tetrahydro-1-naphthol, 0.8 g of 0,5% palladium on calcium carbonate, 0.8 g 5% palladium on charcoal and 1000 ml of ethyl acetate is submitted to hydrogenation at atmospheric pressure and room temperature. After the absorption of 1200 ml of hydrogen the catalysts are removed by filtration. The solution is concentrated by evaporation in vacuo of most of the solvent, whereafter the product crystallizes as white crystals melting at 152°–154° C. Yield 95%.

EXAMPLE 8

2,2-Dimethyl-1(2-hydroxyethylidene)-7-methoxy-3-(N-methyl-p-toleune-sulphonamido)-1,2,3,4-tetrahydronaphthalene

A stirred mixture of 149 g of 2,2-dimethyl-7-methoxy-3-(N-methyl-p-toluenesulphonamido)-1,2,3,4-tetrahydro-1-vinyl-1-naphthol, 1200 ml of dioxane and 1380 ml of 0.5 N sulphuric acid is heated until, after 40 minutes, a temperature of 90° C. is reached. The mixture is kept at that temperature during 2.5 hours whereafter it is cooled and extracted three times with chloroform. The chloroform solution is washed with plenty of water and then after being dried, evaporated in vacuo. The residue is dissolved in acetone. From this solution the product separates as white crystals melting at 142°–144° C. Yield 70%.

EXAMPLE 9

2,2-Dimethyl-7-methoxy-3-(N-methyl-p-toluenesulphonamido)-1-[2(tetrahydro-2-pyranyloxy)ethylidene]-1,2,3,4-tetrahydronaphthalene

To a mechanically stirred suspension of 126 g of 2,2-dimethyl-1-(2-hydroxyethylidene)-7-methoxy-3-(N-methyl-p-toluenesulphonamido)-1,2,3,4-tetrahydronaphthalene in 550 ml of 2,3-dihydropyran there is added 5 ml of concentrated hydrochloric acid when under the development of heat a clear solution is being formed.

After the mixture has been kept at 25° C. for 1 hour 400 ml of ether is added followed by an aqueous solution of potassium carbonate in water. The mixture is shaken and the organic layer is dried and evaporated, respectively. The residue is treated with petroleum ether (boiling range 40°–60° C.) which results in the formation of a clear solution covering a semi crystalline layer. From the supernatant a first crop of crystalline product can be secured. The rest can be gathered by dissolving the semi solid mass in boiling ether and cooling the ethereal solution whereupon crystallization of the product takes place. The product melts at 128°–130° C. Yield 80%.

EXAMPLE 10

2,2-Dimethyl-7-methoxy-3-(N-methyl-p-toleuensulphonamido)-1-[2-(tetrahydro-2-pyranyloxy)ethyl]-1,2,3,4-tetrahydronaphthalene 2,2-Dimethyl-7-methoxy-3-(N-methyl-p-toluenesulphonamido)-1-[2-(tetrahydro-2-pyranyloxy)ethyidene]-1,2,3,4-tetrahydronaphthalene (151 g), dissolved in 1100 ml of dioxan is submitted to a catalytic hydrogenation at atmospheric pressure and roomtemperature, the catalyst being 10 g of 5% palladium on charcoal. After some 80 percent of the calculated amount of hydrogen has been consumed, the hydrogen uptake tends to slow down and an additional quantity of 2 g of catalyst is needed to bring the reduction to an end.

The catalyst is removed by filtration and the filtrate is evaporated in vacuo. The residue does not tend to crystallize. It contains a mixture of two stereoisomers of the title product and it is applied without purification in the next synthesis.

EXAMPLE 11

2,2-Dimethyl-1-(2-hydroxyethyl)-7-methoxy-3-(N-methyl-p-toluenesulphonamido)-1,2,3,4-tetrahydronaphthalene 2,2-Dimethyl-1-(2-hydroxyethylidene)-7-methoxy-3-(N-methyl-p-toluenesulphonamido)-1,2,3,4-tetrahydronaphthalene (15.5 g), dissolved in 250 ml of methanol, containing 2.2 ml of triethylamine, is submitted to catalytic hydrogenation, at atmosphere pressure and room temperature, the catalyst being 2.3 g 5% palladium on charcoal, The calculated amount of hydrogen is taken up within 1 hour. The catalyst is removed by filtration and the solvent by evaporation in vacuo. The residue is dissolved in chloroform and the solution is freed from basic material by means of washing with dilute hydrochloric acid and water, respectively. The dried solution is then concentrated in vacuo leaving a mixture containing two stereoisomers of the desired product. This mixture is suitable for further elaboration as described in example 13.

EXAMPLE 12

2,2-Dimethyl-1-(2-hydroxyethyl)-7-methoxy-3-methylamino-1,2,3,4-tetrahydronaphthalene hydrochloride A solution of 121.5 g of 2,2-dimethyl-7-methoxy-3-(N-methyl-p-toluenesulphonamido)-1-[2-(tetrahydro-2-pyranyloxy)ethyl]-1,2,3,4-tetrahydronaphthalene in 300 ml of absolute ether and 5 ml of dry dioxane is added dropwise to 1500 ml of liquid ammonia which is stirred mechanically. At the same time small pieces of sodium (total amount 30 g) are added. After completion of the addition, which takes some 2 hours, the colourless reaction mixture is diluted cautiously with 200 ml of ether whereafter 15 g of ammonium chloride is added and the ammonia is allowed to evaporate. Then water is added and the aqueous layer separated from the organic one. The aqueous solution is shaken twice with ether and the combined organic solutions are extracted with an excess of dilute hydrochloric acid. The acidic aqueous solution is heated on a steambath during 1.5 hours. After cooling, the basic reaction product is set free by the addition of 4 N sodium hydroxide and gathered by extraction with ether. The ethereal solution is dried and evaporated. The product is converted into the hydrochloride by means of ethanolic hydrogen chloride. The crystalline precipitate which is formed has a melting point of 240°–244° C. It is not a single isomer but mixed with a lower melting one. Accordingly, from the mother liquor more soluble and lower melting (205°–210° C.) crystallisates can be obtained. No special attempts are made to achieve a separation of the isomers. The total yield is 76%.

EXAMPLE 13

2,2-Dimethyl-1-(2-hydroxyethyl)-7-methoxy-3-methylamino-1,2,3,4-tetrahydronaphthalene hydrochloride This compound, described already in Example 12, can be prepared in exactly the same way as described in that example if one starts from 2,2-dimethyl-1-(2-hydroxyethyl)-7-methoxy-3-(N-methyl-p-toluenesulphonamido)-1,2,3,4-tetrahydronaphthalene (cf. Example 11). In this case, however, a 2-pyranyloxy group is absent and accordingly the saponification procedure (heating the aqueous acidic solution on a steambath) is not necessary.

In this case the total yield is 73%.

EXAMPLE 14

2,2-Dimethyl-1-(2-hydroxyethyl)-7-methoxy-3-methylamino-1,2,3,4-tetrahydronaphthalene hydrochloride This compound, described already in Examples 12 and 13, can also be prepared as described in Example 13, however, starting from 2,2-dimethyl-1-(2-hydroxyethylidene)-7-methoxy-3-(N-methyl-p-toluenesulfonamido)1,2,3,4-tetrahydronaphthalene. In this case, both the reduction of the olefinic double bond and the reductive cleavage of the p-toluenesulphonamido group are effectuated by the sodium metal dissolving in liquid ammonia. The endpoint of the reduction is reached if the blue colour persists for some 15 minutes. In this case again, a mixture of two stereoisomers is obtained, the total yield being 87% of crystalline hydrochloride.

EXAMPLE 15

2'-Methoxy-2,9,9-trimethyl-6,7-benzomorphan hydrochloride

A mixture of 41 g of 2,2-dimethyl-1-(2-hydroxyethyl)-7-methoxy-3-methylamino-1,2,3,4-tetrahydronaphthalene hydrochloride, as prepared in Example 12, 200 ml of chloroform and 90 ml of thionylchloride is refluxed during 1.5 hours. The mixture is concentrated in vacuo and then diluted with toluene. The toluene is evaporated in vacuo and this procedure of dissolving in toluene and evaporation of the solvent is repeated once. The residue is finally dissolved in chloroform. From this solution a quantity of 18.5 g of a crystalline hydrochloride separates. It melts at 255°–258° C. and is the diastereoisomer of the starting compound having the substituents at positions 1 and 3 in a trans relation (for convenience called "trans halide"). The mother liquor of the crystallizate is shaken with a solution of sodium carbonate in water, and after being dried stripped from solvent in vacuo. The residue is dissolved in petroleum ether (boiling range 40°–60° C.) and this solution is filtered over aluminium oxide. After evaporation of the petroleum ether, the remaining basic material is dissolved in acetone and converted into the hydrochloride by the addition of ethanolic hydrogen chloride. Again the crystals which appear first belong to the "trans halide" but, after their removal by filtration, the desired compound can be secured as a crystalline hydrochloride melting at 235°–238° C. The yield is 33%. The same yields are obtained if the starting material is prepared according to either example 12 or 13. But if, instead, the starting compound is obtained as described in example 14 the yield of the benzomorphan is 60%.

In this case apparently the ratio between the cis and the trans halide is more favourable.

EXAMPLE 16

9,9-Dimethyl-2'-methoxy-6,7-benzomorphan

To a solution of 29 g of 2'-methoxy-2,9,9-trimethyl-6,7-benzomorphan in 260 ml of dry chloroform there is added a solution of 21 g of cyanogen bromide in 260 ml of dry chloroform. The mixture is heated at reflux temperature for 5 hours, whereupon the solvent is evaporated in vacuo. The residue is dissolved in benzene and basic material is removed by shaking with 4 N hydrochloric acid and then with water. The benzene is evaporated and the residue is thereupon refluxed with a mixture of 380 ml of acetic acid and 1100 ml of 2 N hydrochloric acid. The resulting clear solution is evaporated in vacuo to a volume of about 100 ml and then made alkaline with aqueous ammonia. The base which separates is extracted from the mixture with ether. On concentration the ethereal solution to a small volume the desired compound separates as white crystals melting at 116°–119° C. The hydrochloride can be obtained from a solution of the base in acetone by the addition of ethanolic hydrogen chloride. It melts at 182°–184° C. Yield 54%.

EXAMPLE 17

9,9-Dimethyl-2'-hydroxy-6,7-benzomorphan

A solution of 5.8 g of 9,9-dimethyl-2'-methoxy-6,7-benzomorphan in 40 ml of 47% hydrobromic acid is refluxed during 2 hours. After cooling, the hydrobromide of the desired compound forms a crystalline precipitate which, after recrystallization from a mixture of isopropanol and methanol, melts at 310°–315° C. White crystals. Yield 87%.

The free base can be obtained by shaking a suspension of the hydrobromide in aqueous ammonia with a mixture consisting of 4 parts of chloroform to 1 part of 1-butanol. On evaporation in vacuo the organic extract leaves the product as white crystals melting at 190°–192° C.

EXAMPLE 18

2'-Hydroxy-2,9,9-trimethyl-6,7-benzomorphan

In a manner similar to the method described in example 17, however, starting from 2'-methoxy-2,9,9-trimethyl-6,7-benzomorphan, the above mentioned compound is obtained. It crystallizes from petroleum ether (boiling range 40°–60° C.) and melts at 175°–177° C. Yield 80%. This compound is also obtained as the hydrochloride. It melts at 255°–257° C. with decomposition.

EXAMPLE 19

2-Butyl-9,9-dimethyl-2'-hydroxy-6,7-benzomorphan hydrochloride

To a cooled and stirred solution of 0.6 g of the hydrobromide of 9,9-dimethyl-2'-hydroxy-6,7-benzomorphan in 10 ml of dry pyridine there is added dropwise 1.5 ml of butyric anhydride. The mixture is kept at room temperature for 15 minutes and then at 100° C. for 1 hour when it is taken to dryness. The residue is taken up in ether and washed with water, dilute hydrochloric acid and again water, respectively. The solution is then dried and evaporated leaving a residue consisting of the O,N-diacylated product. A solution of this product in 10 ml of absolute ether is added dropwise to a stirred suspension of 0.7 g of lithium aluminium hydride in 15 ml of absolute ether. The reaction mixture is refluxed during 2 hours, whereupon after cooling, 25 ml of wet ether and subsequently 10 ml of water is added cautiously. The obtained suspension is filtered and the filter cake is washed with chloroform. The filtrate is dried and evaporated in vacuo. The product is converted into the hydrochloride which, after recrystallization from isopropanol melts at 239°–241° C. Yield 76%.

EXAMPLE 20

9,9-Dimethyl-2'-hydroxy-2-propyl-6,7-benzomorphan hydrochloride

In a manner similar to the method described in example 19, however, applying propionic anhydride as the acylating agent, the above-mentioned compound is obtained as the hydrochloride. It melts at 238°–240° C. after recrystallization from 2-butanone. Yield 34%.

EXAMPLE 21

9,9-Dimethyl-2-ethyl-2'-hydroxy-6,7-benzomorphan hydrochloride

In a manner similar to the method described in example 19, however, applying acetic anhydride as the acylating agent, the above-mentioned product is obtained as the hydrochloride melting at 218°–220° C. after recrystallization from 2-butanone. Yield 36%.

EXAMPLE 22

9,9-Dimethyl-2'-hydroxy-2-pentyl-6,7-benzomorphan hydrochloride

In a manner similar to the method described in Example 19, however, applying pentanoylchloride as the acylating agent, the above-mentioned compound is obtained as the hydrochloride melting at 245°–247° C. after recrystallization from 2-butanone. Yield 54%.

EXAMPLE 23

9,9-Dimethyl-2-hexyl-2'-hydroxy-6,7-benzomorphan hydrochloride

In a manner similar to the method described in Example 19, however, applying hexanoyl chloride as the acylating agent the above-mentioned compound is prepared. Its hydrochloride melts at 215°–218° C. (after recrystallization from acetone). Yield 36%.

EXAMPLE 24

2-Cyclopropylmethyl-9,9-dimethyl-2'-hydroxy-6,7-benzomorphan hydrobromide

In a manner similar to the method described in Example 19, however, applying cyclopropanecarbonyl chloride as the acylating agent the above-mentioned product is obtained. It is secured as the hydrobromide which, after recrystallization from isopropanol melts at 254°–256° C. Yield 56%.

EXAMPLE 25

2-Cyclobutylmethyl-9,9-dimethyl-2'-hydroxy-6,7-benzomorphan hydrochloride

In a manner similar to the method described in Example 19, however, applying cyclobutanecarbonyl chloride as the acylating agent the above-mentioned compound is obtained as the hydrochloride which, after recrystallization from a mixture of methanol and isopropanol melts at 293°–296° C. Yield 74%.

EXAMPLE 26

9,9-Dimethyl-2'-hydroxy-2-(3-methyl-2-butenyl)-6,7-benzomorphan hydrochloride

To a mechanically stirred mixture of 0.3 g of 9,9-dimethyl-2'-hydroxy-6,7-benzomorphan hydrobromide, 1.2 g of potassium carbonate and 15 ml of 2-butanone there is added 0.6 ml of 1-bromo-3-methyl-2-butene. After the mixture has been heated at reflux temperature for 2 hours, the solvent is evaporated and the residue is treated with ether and water. The ether layer is extracted three times with 1 N hydrochloric acid. After 24 hours at room temperature the aqueous solution is basified by the addition of aqeous ammonia (25%) and extracted with ether. The residue from the dried and evaporated ethereal solution is treated with acetone and ethanolic hydrogen chloride, whereupon the product crystallizes as the hydrochloride. It melts at 280°–282° C. with decomposition. Yield 80%.

EXAMPLE 27

2-Allyl-9,9-dimethyl-2'-hydroxy-6,7-benzomorphan hydrochloride

A mixture of 2.1 g of 9,9-dimethyl-2'-hydroxy-6,7-benzomorphan hydrobromide, 3.1 g of potassium carbonate, 0.73 ml of allyl bromide and 30 ml of dimethylformamide is heated at 70° C. during 30 minutes. After cooling the mixture is diluted with water and extracted with ether. The ethereal solution is extracted three times with 1 N hydrochloric acid. After evaporation of the acid aqueous extract, the residue is treated with isopropanol, whereupon the product crystallizes as the hydrochloride melting at 218°–220° C. Yield 58%.

EXAMPLE 28

2-(3-Butenyl)-9,9-dimethyl-2'-hydroxy-6,7-benzomorphan hydrochloride

In a manner similar to the method described in example 26, however, applying 1-bromo-2-butene as the alkylating agent the above-mentioned compound is obtained as the hydrochloride. It is recrystallized from isopropanol and melts at 213°–215° C. Yield 71%.

EXAMPLE 29

9,9-Dimethyl-2'-hydroxy-2-propargyl-6,7-benzomorphan hydrochloride

In a manner similar to the method described in example 26, however, applying propargyl chloride as the alkylating agent, the above-mentioned compound is obtained as the hydrochloride which is purified by recrystallization from a mixture of methanol and isopropanol. It melts at 225°–228° C. Yield 60%.

EXAMPLE 30

9,9-Dimethyl-2'-hydroxy-2-(2-phenylethyl)-6,7-benzomorphan hydrochloride

In a manner similar to the method described in example 19, however, applying phenylacetyl chloride as the acylating agent, the above-mentoned compound is obtained as the hydrochloride. It melts at 245°–248° C. Yield 41%.

EXAMPLE 31

2-Cyclobutylmethyl-9,9-dimethyl-2'-methoxy-6,7-benzomorphan hydrobromide

In a manner similar to the method described in example 19, however, starting from 9,9-dimethyl-2'-methoxy-6,7-benzomorphan and applying cyclobutane carbonylchloride as the acylating agent, the above-mentioned compound is obtained as the hydrobromide. It is recrystallized from isopropanol and melts at 223°–225° C. Yield 80%.

EXAMPLE 32

2-Cyclopropylmethyl-9,9-dimethyl-2'-methoxy-6,7-benzomorphan hydrobromide

In a manner similar to the method described in example 31, however, applying cyclopropane carbonylchloride as the acylating agent, the above-mentioned compound is obtained as the hydrobromide. The product melts at 197°–199° C. Yield 40%.

EXAMPLE 33

9,9-Dimethyl-2-ethyl-2'-methoxy-6,7-benzomorphan hydrochloride

In a manner similar to the method described in example 31, however, applying acetic anhydride as the acylating agent, the above-mentioned compound is prepared as the hydrochloride. It is crystallized from acetone and melts at 236°–239° C. Yield 44%.

EXAMPLE 34

9,9-Dimethyl-2'-methoxy-2-propyl-6-7-benzomorphan hydrochloride

In a manner similar to the method described in example 31, however, applying propionic anhydride as the acylating agent, the above-mentioned compound is obtained as the hydrochloride and crystallized from acetone Melting point 188°–191° C. Yield 52%.

EXAMPLE 35

9,9-Dimethyl-2'-methoxy-2-(3-methyl-2-butenyl)-6,7-benzomorphan hydrochloride

In a manner similar to the method described in example 26, however, using 9,9-dimethyl-2'-methoxy-6,7-benzomorphan as the starting material, the above-mentioned compound is obtained as the hydrochloride. It crystallizes from acetone and melts at 191°–194° C. Yield 25%.

EXAMPLE 36

9,9-Dimethyl-2'-methoxy-2-(2-phenylethyl)-6,7-benzomorphan hydrochloride

In a manner similar to the method described in example 35, however, using 2-phenylethyl bromide as the alkylating agent the above-mentioned compound is obtained. In this case the completion of the alkylation required the reaction mixture to be refluxed for 5 hours. The hydrochloride of the product is recrystallized from methanol and melts at 216°–218° C. Yield 61%.

EXAMPLE 37

2-Allyl-9,9-dimethyl-2'-methoxy-6,7-benzomorphan hydrobromide

In a manner similar to the method described in example 27, however, starting from 9,9-dimethyl-2'-methoxy-6,7-benzomorphan and applying allyl bromide as the alkylating agent the above-mentioned product is obtained as the hydrobromide. It is recrystallized from acetone. It melts at 211°–212° C. Yield 70%.

EXAMPLE 38

2-Cyclopentyl-9,9-dimethyl-2'-methoxy-6,7-benzomorphan oxalate

In a manner similar to the method described in example 26, however, using 9,9-dimethyl-2'-methoxy-6,7-benzomorphan as the starting material and cyclopentyl bromide as the alkylating agent the above-mentioned compound is prepared. In this case, however, the alkylation requires more drastic conditions and, accordingly, the mixture is heated during 15 hours at 70°–100° C. in a glass autoclave. The product is secured as the acid oxalate which, after crystallization from acetone melts at 196°–198° C. with decomposition. Yield 41%.

EXAMPLE 39

2-Cyclopentyl-9,9-dimethyl-2'-hydroxy-6,7-benzomorphan

A solution of 250 mg of 2-cyclopentyl-9,9-dimethyl-2'-methoxy-6,7-benzomorphan oxalate in 10 ml of 47% hydrobromic acid is boiled for 1 hour. After cooling the mixture is diluted with water, made alkaline by the addition of aqueous ammonia and extracted with ether. The dried and then evaporated ethereal solution leaves the desired product which crystallizes from petroleum ether (boiling range 40°–60° C.). It melts at 132°–135° C. Yield 40%.

EXAMPLE 40

2'-Acetoxy-2,9,9-trimethyl-6,7-benzomorphan oxalate

A solution of 328 mg of 2'-hydroxy-2,9,9-trimethyl-6,7-benzomorphan in 1.5 ml of acetic anhydride is heated at 100° C. during 20 minutes. Then the mixture is diluted with water and heated at 100° C. for 1 hour. After cooling, the solution is made alkaline by means of aqueous ammonia and extracted with ether. After evaporation of the dried ethereal solution the product is converted into the acid oxalate which crystallizes from acetone. It melts at 185°–189° C. with decomposition. Yield 80%.

EXAMPLE 41

2'-Propionyloxy-2,9,9-trimethyl-6,7-benzomorphan oxalate

In a manner similar to the method described in example 40, however, applying propionic anhydride as the acylating agent the above-mentioned product is obtained as the acid oxalate which is recrystallized from isopropanol. It melts at 151°–154° C. with decomposition. Yield 69%.

EXAMPLE 42

2'-Benzoyloxy-2,9,9-trimethyl-6,7-benzomorphan oxalate

To a cooled and stirred solution of 400 mg of 2'-hydroxy-2,9,9-trimethyl-6,7-benzomorphan in 6 ml of pyridine there is added 0.21 ml of benzoyl chloride. After the mixture is left at room temperature for 15 minutes and then heated at 100° C. for 1 hour, it is evaporated in vacuo. The residue is treated with aqueous ammonia and ether. The dried and then evaporated ethereal solution leaves the product as a non-crystalline base which is converted into the acid oxalate by the addition of oxalic acid to a solution of the base in acetone. It melts at 205°–208° C. with decomposition. Yield 82%.

EXAMPLE 43

2'-Nicotinoyloxy-2,9,9-trimethyl-6,7-benzomorphan oxalate

In a manner similar to the method described in example 42, however, applying nicotinoyl chloride as the acylating agent, the above-mentioned product is obtained as the acid oxalate, crystallizing from acetone and melting at 192°–196° C. with decomposition. Yield 70%.

EXAMPLE 44

(+) and (−) 9,9-Dimethyl-2'-methoxy-6,7-benzomorphan

Racemic 9,9-dimethyl-2'-methoxy-6,7-benzomorphan is obtained as the free base by dissolving the hydrochloride (3.6 g) in water, making the solution alkaline with aqueous sodium hydroxyde and extracting the base with ether. The dried ethereal solution leaves after evaporation 3.19 g of the free base. This is dissolved in 35 ml of hot ethanol whereafter a solution of 2 g of (+) tartaric acid in 3 ml of water is added. The mixture is left at room temperature for some time when 1.5 g of a crystalline salt separates. After recrystallization from a mixture of methanol and water the yield of this salt amounts to 1.02 g. It melts at 186°–187° C. Its optical rotation is $\alpha_D^{21} = + 1.91°$ (2% in water). This salt is the acid (+) tartrate of (+) 9,9-dimethyl-2'-methoxy-6,7-benzomorphan, called for convenience the (++) tartrate.

The mother liquors are evaporated, the residue taken up in water and the free base liberated in a manner as described above. It amounts to 2.2 g. This is dissolved in 30 ml of hot ethanol whereafter 1.43 g of (−) tartaric acid, dissolved in 5 ml of water is added. At room temperature a precipicate of the acid (− −) tartrate (1.95 g) is formed. Recrystallization from a mixture of water and methanol gives 1.66 g of the pure salt with $\alpha_D^{21} = -1.90°$ (2% in water) and melting at 186°–187° C.

Both enantiomers are prepared from their proper salts by treating the aqueous solutions with dilute aqueous sodium hydroxyde and extracting the bases by means of ether. From 1 g of the (− −) salt 0.6 g of the non crystalline base is obtained having $\Delta_D^{21} = -2.31°$ (2% in methanol). The (++) salt gives the (+) enantiomer with $\alpha_D^{21} = +2.49°$ (2% in methanol).

EXAMPLE 45

(−) 9,9-Dimethyl-2'-hydroxy-6,7-benzomorphan hydrobromide

A solution of 0.6 g of (−) 9,9-dimethyl-2'-methoxy-6,7-benzomorphan in 10 ml of 47% hydrobromic acid is boiled during 45 minutes and then evaporated in vacuo. The residue is dissolved in isopropanol and the solvent evaporated. This procedure is repeated twice when the hydrobromide finally crystallizes from isopropanol. It melts at 262°–265° C. with decomposition. $[\alpha]_D^{24} = -106°$ (2% in methanol). Yield 86%.

EXAMPLE 46

(+) 9,9-Dimethyl-2'-hydroxy-6,7-benzomorphan hydrobromide

This compound is made from (+) 9,9-dimethyl-2'-methoxy-6,7-benzomorphan in exactly the same way as described in example 45. The hydrobromide melts at 267°–268.5° C. with decomposition. $[\alpha]_D^{24} = +107°$ (2% in methanol). Yield 84%.

EXAMPLE 47

(−) 2-Cyclopropylmethyl-9,9-dimethyl-2'-hydroxy-6,7-benzomorphan hydrochloride

To a stirred and cooled solution of 0.32 g (−) 9,9-dimethyl-2'-hydroxy-6,7-benzomorphan hydrobromide in 5 ml of pyridine there is added 0.4 ml of cyclopropane carbonylchloride. The reaction mixture is heated at 100° C. for 1 hour and then evaporated to dryness. The residue is treated with water and ether and the ethereal solution thus obtained is washed with 0.5 N hydrochloric acid. The residue (0.4 g) of the dried, evaporated ethereal solution is dissolved in 10 ml of absolute ether. This solution is added to a suspension of 0.4 g of lithium aluminum hydride in 15 ml of absolute ether. The reaction mixture is refluxed for 2 hours, then cooled, whereafter wet ether and subsequently water is added carefully.

The obtained suspension is filtered and the filtercake is rinsed thoroughly with chloroform. The filtrate is evaporated in vacuo and the product isolated as the hydrochloride. It crystallizes from acetone and melts at 254°–256° C. with decomposition. $[\alpha]_D^{24} = -174°$ (2% in methanol). Yield 81%.

EXAMPLE 48

(+) 2-Cyclopropylmethyl-9,9-dimethyl-2'-hydroxy-6,7-benzomorphan hydrochloride

In a manner similar to the method described in example 47, however, using (+) 9,9-dimethyl-2'-hydroxy-6,7-benzomorphan hydrobromide as the starting material, the above-mentioned product is obtained. It crystallizes from acetone and melts at 254°–256° C. under decomposition. $[\alpha]_D^{24} = +172.5°$ (2% in methanol). Yield 60%.

EXAMPLE 49

(−) 2-Allyl-9,9-dimethyl-2'-hydroxy-6,7-benzomorphan hydrochloride

In a manner similar to the method described in example 27, however, starting from (−) 9,9-dimethyl-2'-hydroxy-6,7-benzomorphan hydrobromide the above-mentioned compound is obtained as the hydrochloride. It is recrystallized from a mixture of methanol and 2-butanone and melts at 220°–221° C. with decomposition. $[\alpha]_D^{29} = -172.5°$ (2% in methanol). Yield 58%.

EXAMPLE 50

(−) 2'-Hydroxy-2,9,9-trimethyl-6,7-benzomorphan

To a solution of 0.4 g of (−) 9,9-dimethyl-2'-hydroxy-6,7-benzomorphan in 15 ml of dry benzene there is added, with stirring, 1 g of potassium hydrogen carbonate and 0.4 ml of ethyl chloroformate.

The mixture is refluxed during 45 minutes, then cooled and washed with water and dilute hydrochloric acid. Evaporation of the benzene in vacuo leaves a residue which, after being dissolved in 10 ml of absolute ether, is added to a suspension of 0.5 g of lithium aluminum hydride in 15 ml of absolute ether. The reaction mixture is refluxed during 2 hours and after being cooled treated with wet ether and water as usually. Further processing occurs as described in example 47. In this case, however, the free base itself is secured as white crystals, obtained from petroleum ether (boiling range 40°–60° C.). It melts at 106°–108° C. Yield 51%. $[\alpha]_D^{27} = -162°$ (1% in methanol).

EXAMPLE 51

(+) 2'-Hydroxy-2,9,9-trimethyl-6,7-benzomorphan

In a manner similar to the method described in example 50, however, starting from (+) 9,9-dimethyl-2'-hydroxy-6,7-benzomorphan the above-mentioned compound is obtained. It crystallizes from petroleum ether (boiling range 40°–60° C.) and melts at 105°–107° C., the optical rotation being $[\alpha]_D^{28} = +161°$ (1% in methanol). Yield 69%.

EXAMPLE 52

9,9-Dimethyl-2-furfuryl-2'-hydroxy-6,7-benzomorphan hydrochloride

In a manner similar to the method described in example 19, however, applying 2-furoyl chloride as the acylating agent, the above-mentioned compound is obtained as the hydrochloride.

It melts at 227°–230° C. with decomposition (after recrystallization from a mixture of methanol and 2-butanone). Yield 75%.

EXAMPLE 53

9,9-Dimethyl-2'-hydroxy-2-(2-methyl-3-furylmethyl)-6,7-benzomorphan hydrochloride In a manner similar to the one described in example 19, however, applying 2-methyl-3-furoyl chloride as the acylating agent, the above-mentioned compound is obtained as the hydrochloride.

After recrystallization from isopropanol it melts at 256°–258° C. with decomposition. Yield 98%.

EXAMPLE 54

9,9-Dimethyl-2-(3-furylmethyl)-2'-hydroxy-6,7-benzomorphan hydrochloride

In a manner similar to the method described in example 19, however, applying 3-furoyl chloride as the acylating agent, the above-mentioned compound is obtained as the hydrochloride (from acetone).

It melts at 277°–279° C. with decomposition. Yield 50%.

EXAMPLE 55

9,9-Dimethyl-2'-hydroxy-2-(3-methylfurfuryl)-6,7-benzomorphan hydrochloride

In a manner similar to the method described in example 19, however, applying 3-methyl-2-furoyl chloride as the acylating agent, the above-mentioned compound is obtained as the hydrochloride (from acetone). It melts at 207°-209° C. with decomposition. Yield 70%.

EXAMPLE 56

2-(1-Cyclohexen-1-yl-methyl)-9,9-dimethyl-2'-hydroxy-6,7-benzomorphan, hydrochloride In a manner similar to the method described in example 27, however, applying 1-chloromethylcyclohexene as the alkylating agent, the above-mentioned compound is obtained as the hydrochloride from acetone. It melts at 265° C. with decomposition. Yield 75%.

EXAMPLE 57

2-(2-Cyclohexiliden-ethyl)-9,9-dimethyl-2'-hydroxy-6,7-benzomorphan, hydrochloride In a manner similar to the one described in example 27, however, applying (2-chloro-ethylidene)-cyclohexane as the alkylating agent, the above mentioned compound is obtained as the hydrochloride. It is crystallized from a mixture of isopropanol and acetone. It melts at 210° C. with decomposition. Yield 70%.

EXAMPLE 58

2-(2-Chloro-allyl)-9,9-dimethyl-2'-hydroxy-6,7-benzomorphan, hydrochloride

In a manner similar to the method described in example 27, however, applying 2,3-dichloropropene as the alkylating agent, the above mentioned compound is obtained as the hydrochloride. It crystallizes from a mixture of acetone and isopropanolic hydrogen chloride. It melts at 235° C. with decomposition. Yield 95%.

EXAMPLE 59

2-(2-Cyclohexen-1-yl)-9,9-dimethyl-2'-hydroxy-6,7-benzomorphan, hydrochloride

In a manner similar to the method described in example 27, however, applying 3-bromocyclohexene as the alkylating agent, the above mentioned compound is obtained as the hydrochloride, crystallized from a mixture of methanol, acetone and ethyl acetate. It melts at 80° C. with decomposition. Yield 49%.

EXAMPLE 60

9,9-Dimethyl-2'-hydroxy-2-tetrahydrofurfuryl-6,7-benzomorphan, hydrobromide

In a manner similar to the one described in example 27, however, applying tetrahydrofurfuryl bromide as the alkylating agent, the above-mentioned compound is obtained as the major component from a mixture of two possible diastereo isomeric products. It is obtained as the hydrobromide and recrystallized from a mixture of methanol and ethylacetate. It melts at 163°-165° C. with decomposition. Yield 47%.

EXAMPLE 61

2-(3-Bromo-3-methyl-butyl)-9,9-dimethyl-2'-hydroxy-6,7-benzomorphan, hydrobromide In a manner similar to the method described in example 27, however, applying 3-methyl-2-butenyl bromide as the alkylating agent and subsequently heating the obtained 9,9-dimethyl-2'-hydroxy-2-(3-methyl-2-butenyl)-6,7-benzomorphan in a small quantity of hydrobromic acid at 90° C., the above mentioned compound is obtained as the hydrobromide, crystallized from acetone. It melts at 208°-209° C. with decomposition. Yield 45%.

TEST-REPORT

Tests were conducted with respect to the pharmacological properties of various 6,7-benzomorphans according to this invention which are included within general formula I above, and in which the substituents R, $R_1$ and $R_2$ are as indicated in the below Table A.

The tests conducted were as follows:

Tail Withdrawal Test In Rats

The analgesic potency of the tested compounds was determined by the so-called tail withdrawal test in rats having a body weight of 250 ± 10 g. substantially in accordance with the standard procedures described by Janssen P. A. J., Niemegeers C. J. E. and Dony J. G. H.; Arzneim-Forsch, 13, 502 (1963). The test procedures were substantially as described, with the exceptions that measurements were made more frequently, the cut-off time was reduced from 15 seconds to 10 seconds, and the results were rated according to three different levels of analgesia, defined as follows:

a. Moderate analgesia (M.A. on Table A) — the tail withdrawal reaction time is $>6$ and $<10$ seconds.

b. Pronounced analgesia (P.A. on Table A) — no tail withdrawal response over a reaction time $>10$ seconds, but slight movements of the tail in the warm water cup.

c. Surgical analgesia (S.A. on Table A) — no tail withdrawal response over a reaction time $>10$ seconds, and no movements or reaction of the tail.

Table A gives the dosages, in mg./kg of body weight, administered subcutaneously that constitute the $ED_{50}$-values and confidence limits for each of the defined compounds to achieve the above defined levels of analgesia (M.A., P.A. and S.A.). For purposes of comparison, Table A also gives the corresponding values for Nalorphine and Pentazocine.

Nalorphine-like Activity In Rats

In order to test the Nalorphine-like activity of the tested compounds, that is, the potency of such compounds in reversing the respiratory depression, loss of righting reflex, muscular rigidity, surgical analgesia and blockage of the corneal and pinna reflexes resulting from the administration of high doses of fentanyl, Wistar rats were given a subcutaneous injection of 0.63 mg/kg body weight of fentanyl to induce the described phenomena. 30 minutes after the fentanyl dose, the same animals received intravenous injections of the identified test compounds and of Nalorphine and Pentazocine for comparison purposes. Table A indicates the $ED_{50}$ in mg/kg body weight, exhibiting nalorphine-like properties, that is, capable of immediately reversing the mentioned phenomena induced by the dosage of fentanyl.

Writhing Test In Rats

Wistar rats were injected with ½ ml of a 1 percent-solution of acetic acid I.P. and the number of writhings during the 30 minutes following the injection were noted. The various test compounds identified on Table A, and also Nalorphine and Pentazocine for the purposes of comparison, were administered subcutaneously 30 minutes prior to the standard injection of acetic acid. Table A gives, for each test compound, the $ED_{50}$ in mg/kg body weight, that reduced the number of writhings by 50% in the 30 minutes following the acetic acid injection.

TABLE A

| $R_1$ | $R_2$ | R | α | Base salt | Tail withdrawal test M.A. | P.A. | S.A. | Nalorphine like activity | Writhing test |
|---|---|---|---|---|---|---|---|---|---|
| H | OH | $CH_3$ | ± | HBr | >2.2 | >2.2 | >2.2 | >2.2 | ~3.6 |
| $CH_3$ | OH | $CH_3$ | ± | HCl | 0.62 | 1.14 | >2.2 | 0.42 | 0.024 |
| $CH_3$ | OH | $CH_3$ | — | — | 0.53 | 1.78 | >2.2 | 0.13 | 0.04 |
| $CH_3$ | OH | $CH_3$ | + | — | >2.2 | >2.2 | >2.2 | >2.2 | >3.2 |
| $C_2H_5$ | OH | $CH_3$ | ± | HCl | — | >2.2 | — | 0.054 | >3.2 |
| n-$C_3H_7$ | OH | $CH_3$ | ± | HCl | >2.2 | >2.2 | >2.2 | 0.004 | >3.2 |
| n-$C_3H_7$ | OH | $CH_3$ | — | HCl | — | >2.2 | — | 0.0032 | >3.2 |
| n-$C_4H_9$ | OH | $CH_3$ | ± | HCl | — | >2.2 | — | 0.062 | >3.2 |
| n-$C_5H_{11}$ | OH | $CH_3$ | ± | HCl | >21.5 | >21.5 | >21.5 | 0.52 | 1.41 |
| n-$C_6H_{13}$ | OH | $CH_3$ | ± | HCl | — | >2.2 | — | >2.2 | 2.75 |
| $CH_2-CH_2-\overset{Br}{\underset{\phantom{x}}{C}}(CH_3)_2$ | OH | $CH_3$ | ± | HBr | — | — | — | 0.076 | 0.52 |
| $CH_2-CH=CH_2$ | OH | $CH_3$ | ± | HCl | >2.2 | >2.2 | >2.2 | 0.004 | >3.2 |
| $CH_2-CH=CH_2$ | OH | $CH_3$ | — | HCl | >2.2 | >2.2 | >2.2 | 0.003 | >3.2 |
| $CH_2-CH=CH-CH_3$ | OH | $CH_3$ | — | HCl | — | >2.2 | — | 0.0056 | >3.2 |
| $CH_2-CH=C(CH_3)_2$ | OH | $CH_3$ | ± | HCl | — | >2.2 | — | 0.46 | >3.2 |
| $CH-\overset{Cl}{\underset{\phantom{x}}{C}}=CH_2$ | OH | $CH_3$ | ± | HCl | — | >2.2 | — | 0.156 | >31.6 |
| $CH_2-CH_2-CH=CH_2$ | OH | $CH_3$ | ± | HCl | >2.2 | >2.2 | >2.2 | 0.023 | >3.2 |
| $CH_2-CH_2-CH=CH_2$ | OH | $CH_3$ | — | HCl | — | >2.2 | — | 0.0084 | >3.2 |
| $CH_2-C\equiv CH$ | OH | $CH_3$ | ± | HCl | >2.2 | >2.2 | >2.2 | 0.012 | >3.2 |
| $CH_2-C\equiv CH$ | OH | $CH_3$ | — | HCl | — | — | — | 0.003 | >3.2 |
| $CH_2$-(furan) | OH | $CH_3$ | ± | HCl | >2.2 | >2.2 | >2.2 | 0.007 | >3.2 |
| $CH_2$-(furan) | OH | $CH_3$ | — | HCl | >2.2 | >2.2 | >2.2 | 0.0017 | >3.2 |
| $CH_3$-(furan)-$CH_2$ | OH | $CH_3$ | ± | HCl | >2.2 | >2.2 | >2.2 | 0.31 | 1.2 |
| $CH_2$-(furan) | OH | $CH_3$ | ± | HCl | >2.2 | >2.2 | >2.2 | 0.009 | >3.2 |
| $CH_2$-(furan)-$CH_3$ | OH | $CH_3$ | ± | HCl | ~2.2 | >2.2 | >2.2 | 1.02 | >3.2 |
| $CH_2$-(furan) | OH | $CH_3$ | ± | HBr | — | — | — | 0.015 | 0.13 |
| $CH_2$-(cyclopropyl) | OH | $CH_3$ | ± | HBr | >2.2 | >2.2 | >2.2 | 0.006 | >3.2 |
| $CH_2$-(cyclopropyl) | OH | $CH_3$ | — | HCl | >2.2 | >2.2 | >2.2 | 0.001 | >3.2 |
| $CH_2$-(cyclopropyl) | OH | $CH_3$ | + | HCl | >2.2 | >2.2 | >2.2 | >2.2 | >3.2 |
| $CH_2$-(cyclobutyl) | OH | $CH_3$ | ± | HCl | >2.2 | >2.2 | >2.2 | 0.028 | 0.60 |
| (cyclopentyl) | OH | $CH_3$ | ± | — | >2.2 | >2.2 | >2.2 | 0.41 | 1.4 |
| (cyclohexyl) | OH | $CH_3$ | ± | HCl | — | >2.2 | — | 0.066 | 10.1 |
| $CH_2-CH_2$-(phenyl) | OH | $CH_3$ | ± | HCl | — | 0.24 | — | — | — |
| $CH_2-CH=CH_2$ | $OCH_3$ | $CH_3$ | ± | HBr | — | >2.2 | — | 1.62 | >3.2 |

TABLE A-continued

| $R_1$ | $R_2$ | R | $a$ | Base salt | Tail withdrawal test M.A. | Tail withdrawal test P.A. | Tail withdrawal test S.A. | Nalorphine like activity | Writhing test |
|---|---|---|---|---|---|---|---|---|---|
| CH$_2$— | OCH$_3$ | CH$_3$ | ± | HBr | — | >2.2 | — | 0.76 | >3.2 |
| CH$_3$ | OCOCH$_3$ | CH$_3$ | ± | (COOH)$_2$ | — | 0.96 | — | — | — |
| CH$_3$ | OCOC$_2$H$_5$ | CH$_3$ | ± | (COOH)$_2$ | — | 0.96 | — | — | — |
| CH$_3$ | OCO—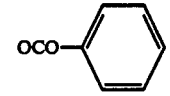 | CH$_3$ | ± | (COOH)$_2$ | — | 1.26 | — | — | — |
| CH$_3$ | OCO—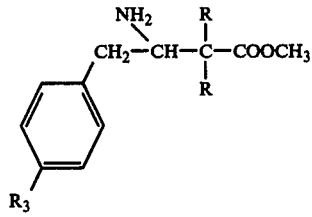 | CH$_3$ | ± | (COOH)$_2$ | — | 0.96 | — | — | — |
| Nalorphine | | | | | 20 | >40 | >40 | 0.16 | 6.6 |
| Pentazocine | | | | | 5.0 | 40 | >160 | 2.2 | 5.6 |

What we claim is:

1. A process for the preparation of a benzomorphan compound of the formula

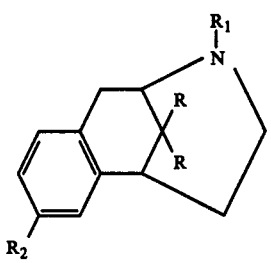 I in which R is selected from the class consisting of methyl or ethyl; R$_1$ is selected from the class consisting of hydrogen atom, alkyl, haloalkyl and alkenyl groups containing up to seven carbon atoms, haloalkenyl and alkinyl groups containing up to four carbon atoms, cycloalkyl and cycloalkenyl groups containing up to seven carbon atoms, cycloalkylalkyl, cycloalkenylalkyl, cycloalkylidenealkyl and aralkyl groups containing up to nine carbon atoms, heteroarylalkyl compounds containing one oxygen atom and up to seven carbon atoms or heterocycloalkylalkyl groups containing one or two oxygen atoms and up to seven carbon atoms; and R$_2$ is selected from the class consisting of hydrogen atom, hydroxy groups, alkoxy groups containing up to three carbon atoms, alkoxyalkoxy groups containing up to four carbon atoms, nicotinoyloxy groups, lower alkanoyloxy groups, phenylalkanoyloxy groups containing up to nine carbon atoms or alkylaroyloxy groups containing up to nine carbon atoms; and pharmaceutically acceptable salts thereof; which comprises:

A. Reacting an aminoacid ester compound of the formula

V $$CH_2-CH-\underset{\underset{R}{|}}{\overset{\underset{NH_2}{|}}{C}}-COOCH_3 \quad \underset{R_3}{\phantom{X}}$$

wherein R is as defined above, and R$_3$ is hydrogen or lower alkoxy, (1) with an acylating agent to form the corresponding acylamino ester compound VI;

(2) alkylating the ester of compound VI to obtain the alkylamido ester compound VII;

(3) saponifying the ester of compound VI or VII to obtain the corresponding acylamino or alkylamido acid compound VIII;

(4) converting the acylamino or alkylamido acid compound VIII to an amidoacyl chloride compound IX;

(5) converting the amidoacyl chloride compound IX by a Friedel-Crafts ring closure reaction to form a naphthalenone compund of the formula

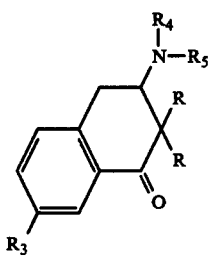 IV wherein R and R$_3$ are as defined above; R$_4$ is an acyl group; and R$_5$ is hydrogen alkyl, cycloalkyl or cycloalkylalkyl;

(a) in the event that R$_5$ is hydrogen in the naphthalenone compound IV, alkylating the latter to convert R$_5$ to the more restricted meaning of alkyl, cycloalkyl or cycloalkylalkyl;

B. Reacting the naphthalenone compound IV (1) with an alkali metal acetylide to obtain an alcohol, ethinyl compound X;

(2) partially reducing the ethinyl group of compound X to obtain an alcohol, ethylene compound XI;

(3) isomerizing compound XI to obtain an hydroxy ethylidene compound XII;

(4) (a) converting the hydroxy ethylidene compound XII by reduction to an hydroxy ethyl compound XIII and deacylating compound XIII to form an aminoalcohol compound XVI; or (b) (1) converting the hydroxy ethylidene compound XII to a tetrahydropyranyl ether compound XIV, reducing the compound XIV to compound XV and deacylating compound XV, followed by hydrolysis to form an aminoalcohol compound XVI; or (2) converting the compound XV by acid hydrolysis to compound XIII and deacylating compound XIII to an aminoalcohol compound XVI; or (c) deacylating and reducing compound XII to form an aminoalcohol compound XVI; and (5) converting the aminoalcohol compound XVI to a tetrahydronaphthalene compound having the formula

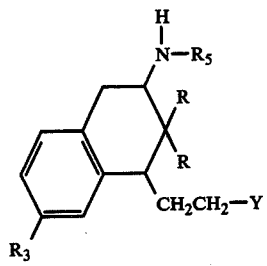

wherein R and $R_3$ are as defined above, $R_5$ has the more restricted meaning defined above, and Y is a halogen; and C. Subjecting the tetrahydronaphthalene to a ring closure in reaction in alkaline medium and treating the resulting closed ring compound to form the desired $R_1$ and/or $R_2$ substituents and/or salt derivatives of compound I, as above defined.

2. The process of claim 1; in which said converting of the hydroxy ethylidene by reduction to an hydroxy ethyl compound XIII is effected in a basic medium.

3. The process of claim 1 which comprises resolving the benzomorphan compound I into optical enantiomers.

4. The process of claim 1 wherein each of R and $R_5$ are methyl.

5. The process of claim 1 wherein $R_4$ is a sulfonyl group.

6. The process of claim 1; in which each of R and $R_5$ is methyl, Y is a halogen, and $R_4$ is a substituted sulfonyl group.

* * * * *